(12) United States Patent
Knitt et al.

(10) Patent No.: US 7,253,641 B2
(45) Date of Patent: Aug. 7, 2007

(54) RADIO FREQUENCY PARTICULATE SENSING SYSTEM

(75) Inventors: Andrew A. Knitt, Deer Creek, IL (US); Mark T. DeCou, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 11/477,860

(22) Filed: Jun. 30, 2006

(65) Prior Publication Data
US 2007/0024289 A1    Feb. 1, 2007

Related U.S. Application Data

(63) Continuation-in-part of application No. 11/393,681, filed on Mar. 31, 2006, which is a continuation-in-part of application No. 11/189,530, filed on Jul. 26, 2005.

(51) Int. Cl.
*G01R 27/04* (2006.01)

(52) U.S. Cl. .................................. 324/639; 324/641

(58) Field of Classification Search ............... 324/639, 324/641, 698
See application file for complete search history.

(56) References Cited

U.S. PATENT DOCUMENTS

| | | |
|---|---|---|
| 4,477,771 A | 10/1984 | Nagy et al. |
| 4,580,441 A | 4/1986 | Sakurai et al. |
| 5,157,340 A | 10/1992 | Walton et al. |
| 5,173,662 A | 12/1992 | Trerice et al. |
| 5,177,444 A | 1/1993 | Cutmore |
| 5,195,317 A | 3/1993 | Nobue et al. |
| 5,369,369 A | 11/1994 | Cutmore |
| 5,423,180 A | 6/1995 | Nobue et al. |
| 5,497,098 A * | 3/1996 | Heil et al. .................. 324/637 |
| 5,497,099 A | 3/1996 | Walton |
| 5,729,470 A | 3/1998 | Baier et al. |
| 6,788,072 B2 | 9/2004 | Nagy et al. |
| 6,964,694 B2 | 11/2005 | Rauchfuss et al. |

(Continued)

FOREIGN PATENT DOCUMENTS

EP    0 506 083    9/1992

(Continued)

*Primary Examiner*—Walter Benson
(74) *Attorney, Agent, or Firm*—Finnegan, Henderson, Farabow, Garrett & Dunner

(57) ABSTRACT

A particulate sensing system for a particulate trap including a radio frequency transmit circuit and a radio frequency receive circuit is disclosed. The transmit circuit may include a wideband signal generator configured to produce a wideband radio frequency signal and a wideband radio frequency amplifier, coupled to the wideband signal generator. The transmit circuit may include a transmit antenna coupled to the wideband radio frequency amplifier and configured to propagate the wideband radio frequency signal through a filter medium. The receive circuit may include a receive antenna configured to receive the wideband radio frequency signal that has been propagated through the filter medium, and a bandpass filter coupled to the receive antenna and configured to limit a frequency range of the received wideband radio frequency signal. The receive circuit may include a radio frequency power sensing device coupled to the bandpass filter and configured to sense a power level of the received wideband radio frequency signal and configured to output a direct current voltage proportional to the total power received across an operating frequency range of the radio frequency power sensing device.

22 Claims, 8 Drawing Sheets

U.S. PATENT DOCUMENTS

2004/0213351 A1* 10/2004 Shattil ........................ 375/260
2007/0019282 A1* 1/2007 Weiner et al. .............. 359/326

FOREIGN PATENT DOCUMENTS

| JP | 6-201362 | 7/1994 |
| JP | 06201362 | 7/1994 |
| WO | WO 00/14518 | 3/2000 |
| WO | WO 2005/093233 | 10/2005 |

* cited by examiner

RADIO FREQUENCY PARTICULATE SENSING SYSTEM

RELATED APPLICATIONS

This is a continuation-in-part of U.S. patent application Ser. No. 11/393,681, filed Mar. 31, 2006, which is a continuation-in-part of pending U.S. patent application Ser. No. 11/189,530, filed Jul. 26, 2005, the entire disclosures of which are incorporated herein by reference.

TECHNICAL FIELD

The present disclosure relates generally to a particulate sensing system, and more particularly, to a radio frequency particulate sensing system.

BACKGROUND

Engines, including diesel engines, gasoline engines, natural gas engines, and other engines known in the art, may exhaust a complex mixture of air pollutants. The air pollutants may include both gaseous and solid material, such as, for example, particulate matter. Particulate matter may include ash and unburned carbon particles and may sometimes be referred to as soot.

Due to increased environmental concerns, among other things, exhaust emission standards may have become more stringent. The amount of particulate matter and gaseous pollutants emitted from an engine may be regulated depending on the type, size, and/or class of engine. In order to meet these emissions standards, engine manufacturers have pursued improvements in several different engine technologies, such as fuel injection, engine management, and air induction, to name a few. In addition, engine manufacturers have developed devices for treatment of engine exhaust after it leaves the engine.

Engine manufacturers have employed exhaust treatment devices called particulate traps to remove the particulate matter from the exhaust flow of an engine. A particulate trap may include a filter designed to trap particulate matter. The use of the particulate trap for extended periods of time, however, may enable particulate matter to accumulate on the filter, thereby causing damage to the filter and/or a decline in engine performance.

One method of restoring the performance of a particulate trap may include regeneration. Regeneration of a particulate trap filter system may be accomplished by thermal regeneration, which may include increasing the temperature of the filter and the trapped particulate matter above the combustion temperature of the particulate matter, thereby burning away the collected particulate matter and regenerating the filter system. This increase in temperature may be effectuated by various means. For example, some systems employ a heating element (e.g., an electric heating element) to directly heat one or more portions of the particulate trap (e.g., the filter material or the external housing). Other systems have been configured to heat the exhaust gases upstream from the particulate trap, allowing the flow of the heated gases through the particulate trap to transfer heat to the particulate trap. For example, some systems may alter one or more engine operating parameters, such as air/fuel mixture, to produce exhaust gases with an elevated temperature. Running an engine with a "rich" air/fuel mixture can elevate exhaust gas temperature. Other systems heat the exhaust gases upstream from the particulate trap, with the use of a burner that creates a flame within the exhaust conduit leading to the particulate trap.

Some systems may be configured to initiate regeneration in response to one or more trigger conditions that may be indicative of significant accumulation of particulate matter in a particulate trap. For example, some systems may include one or more pressure sensors configured to measure "backpressure" in an exhaust system (i.e., pressure in the exhaust system upstream from a particulate trap). Such systems may be configured to initiate regeneration upon detection of a backpressure above a predetermined level, which may indicate significant blockage of exhaust flow due to accumulation of particulate matter in the filter.

Other systems have been developed to measure, estimate, or otherwise detect the amount of particulate matter that has accumulated on a particulate filter. For example, U.S. Pat. No. 5,497,099 (the '099 patent), issued to Walton, describes an apparatus for detecting the accumulation of particulate material on a filter. The apparatus includes an amplitude modulation radio frequency (RF) generator, a transmitter, output and input antennas, and a monitor for measuring the transmission loss through at least a portion of the filter medium.

Although the system of the '099 patent may detect soot in a filter medium, it may use a modulated radio frequency signal. For example, the '099 patent discloses an amplitude modulation (AM) radio frequency generator. Use of modulated radio frequency signals, such as AM, may require additional components and may lead to a more complicated and/or costly system.

The disclosed system is directed to one or more improvements in existing particulate matter detection systems.

SUMMARY OF THE INVENTION

In one aspect, the present disclosure is directed to a particulate sensing system for a particulate trap including a radio frequency transmit circuit and a radio frequency receive circuit. The transmit circuit may include a wideband signal generator configured to produce a wideband radio frequency signal and a wideband radio frequency amplifier, coupled to the wideband signal generator. The transmit circuit may include a transmit antenna coupled to the wideband radio frequency amplifier and configured to propagate the wideband radio frequency signal through a filter medium. The receive circuit may include a receive antenna configured to receive the wideband radio frequency signal that has been propagated through the filter medium, and a bandpass filter coupled to the receive antenna and configured to limit a frequency range of the received wideband radio frequency signal. The receive circuit may include a radio frequency power sensing device coupled to the bandpass filter and configured to sense a power level of the received wideband radio frequency signal and configured to output a direct current voltage proportional to the total power received across an operating frequency range of the radio frequency power sensing device.

In another aspect, the present disclosure is directed to a particulate sensing system for a particulate trap. The particulate sensing system may include a particulate trap including an outer housing and a filter medium. The particulate sensing system may include a radio frequency transmit circuit and a radio frequency receive circuit. The transmit circuit may include a waveform generator configured to generate at least one waveform signal and a sample trigger line coupled to the waveform generator configured to provide a sample trigger signal. The transmit circuit may include a voltage controlled oscillator coupled to the waveform generator and configured to produce a narrowband radio signal having a frequency that is proportional to the waveform signal, and a transmit antenna disposed within the outer housing and adjacent to the filter medium and coupled to the voltage controlled oscillator and configured to propagate the narrowband radio frequency signal through the filter medium. The receive circuit may include a receive antenna disposed in the outer housing opposing the transmit antenna and adjacent to the filter medium, the receive circuit configured to receive the narrowband radio frequency signal propagated through the filter medium, and a bandpass filter coupled to the receive antenna and configured to limit a frequency range of the received narrowband radio frequency signal. The receive circuit may include a radio frequency power sensing device coupled to the bandpass filter and configured to sense a power level of the received narrowband radio frequency signal and configured to provide an output signal proportional to the total power received across an operating frequency range of the radio frequency power sensing device. The receive circuit may include a low pass filter coupled to the radio frequency power sensing device and configured to integrate the output signal; and a sample-and-hold circuit coupled to the low pass filter and the sample trigger line, the sample-and-hold circuit configured to sample an output of the low pass filter using the sample trigger signal, hold the sampled value, and produce an analog signal representing received radio frequency power.

In another aspect, the present disclosure is directed to a method of sensing particulate matter in a particulate trap. The method may include providing a radio frequency transmit circuit including a waveform generator, a sample trigger line, a voltage controlled oscillator, and a transmit antenna, and generating a waveform signal using the waveform generator. The method may include providing a sample trigger signal using the sample trigger line and producing a narrowband radio frequency signal based on the waveform signal using the voltage controlled oscillator. The method may include propagating the narrowband radio frequency signal through a filter medium of the particulate trap using the transmit antenna and providing a radio frequency receive circuit including a receive antenna, a bandpass filter, a radio frequency power sensing device, a low pass filter, and a sample-and-hold circuit. The method may include receiving the narrowband radio frequency signal propagated through the filter medium using the receive antenna and limiting a frequency range of the received narrowband radio frequency signal using the bandpass filter. The method may include sensing a power level of the received narrowband radio frequency signal using the radio frequency power sensing device and providing an output signal proportional to the total power received across an operating frequency range of the radio frequency power sensing device. The method may include integrating the output signal using the low pass filter, and producing an analog signal using the sample-and-hold circuit, the analog signal representing received radio frequency power.

DETAILED DESCRIPTION

Figure 1:
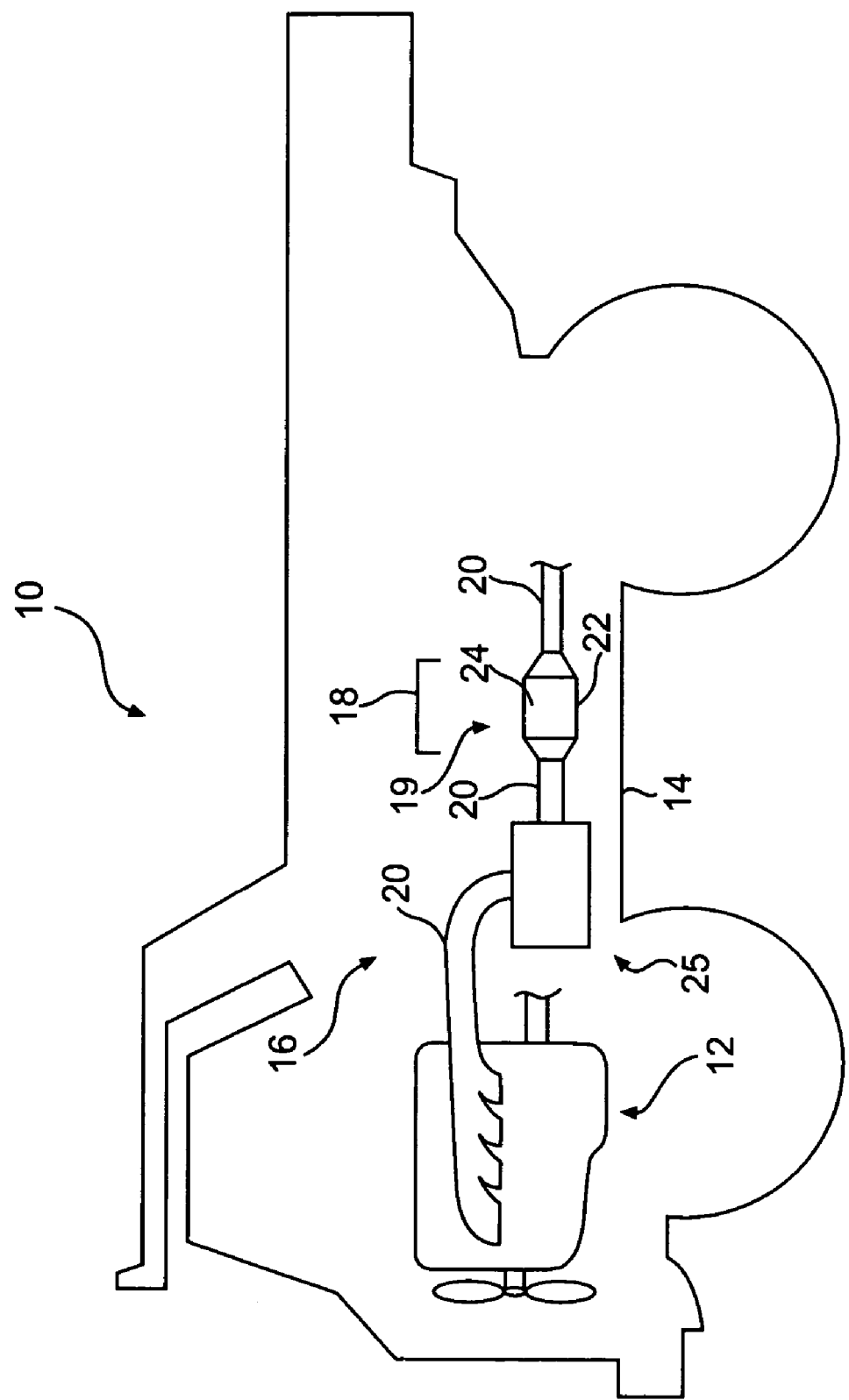
FIG. 1 is a diagrammatic illustration of a machine having a particulate trap regeneration system according to an exemplary disclosed embodiment.

FIG. 1 illustrates a machine 10. Machine 10 may include, an engine 12, which may be mounted to a frame 14, and a particulate trap regeneration system 16. Although machine 10 is shown as a truck, machine 10 could be any type of machine having an exhaust producing engine. Machine 10 may embody a fixed or mobile machine that performs some type of operation associated with an industry such as mining, construction, farming, transportation, or any other industry known in the art. For example, machine 10 may be an earth moving machine such as an excavator, a dozer, a loader, a backhoe, a motor grader, a dump truck (as shown in FIG. 1), or any other earth moving machine.

Engine 12 may be any kind of engine that produces an exhaust flow of exhaust gases. For example, engine 12 may be an internal combustion engine, such as a gasoline engine, a diesel engine, a gaseous fuel burning engine or any other exhaust gas producing engine.

Regeneration system 16 may include an after-treatment device 18. After-treatment device 18 may be any type of device configured to remove one or more constituents from the exhaust flow of engine 12. In some embodiments, after-treatment device 18 may be regenerated by heat or some other measure. In one embodiment, after-treatment device 18 may include a particulate trap 19. Particulate trap 19 may be configured to remove one or more types of particulate matter from the exhaust gases produced by engine 12 and flowing through an exhaust conduit 20 configured to direct all or a portion of the exhaust gases produced by engine 12 to after-treatment device 18. Particulate trap 19 may include an outer housing 22, which may encase a filter medium 24 (e.g. a porous ceramic material, such as cordierite) configured to remove (i.e., trap) one or more types of particulate matter from the exhaust flow of engine 12.

Although after-treatment device 18 is discussed herein primarily as being a particulate trap, in other embodiments, after-treatment device 18 may include multifunctional devices such as a combination of a catalytic converter and a particulate trap in the same unit or a catalytic particulate trap, wherein filter medium 24 may include a catalytic material and/or a catalytic coating.

After-treatment device 18 may be configured to be thermally regenerated. That is, regeneration of after-treatment device 18 may be accomplished by increasing the temperature of after-treatment device 18. Such increases in temperature of after-treatment device 18 may be generated in a number of different ways. For example, heat may be directly applied to after-treatment device 18 via a heating device integral with or adjacent to after-treatment device 18. An example of such a heating device may include an electric heating element (not shown).

Alternatively or additionally, the temperature of after-treatment device 18 may be increased by heat transferred to it from the exhaust gases flowing through it. In such embodiments, heat may be applied to exhaust gases upstream from after-treatment device 18. The temperature of the exhaust gases may be increased in one or more ways. For example, altering engine parameters may have an effect on exhaust gas temperature. Exhaust temperature may also be raised by heating the exhaust gases or exhaust conduit 20. For example, an electric heating element and/or flame or plasma producing burner may be configured to heat the exhaust gases or exhaust conduit 20. In one embodiment, regeneration system 16 may include a regeneration device 25 configured to reduce an amount of particulate matter in after-treatment device 18. For example, regeneration device 25 may include a burner assembly configured to increase the temperature of the exhaust gases flowing through exhaust conduit 20 upstream from after-treatment device 18. Regeneration device 25 may be configured to maintain or restore the performance of after-treatment device 18 through thermal regeneration.

Accumulation of exhaust flow constituents in after-treatment device 18 may result in a decline in engine performance and/or possible damage to after-treatment device 18 and/or other components of regeneration system 16. Regeneration device 25 may be configured to prevent or restore any decline in engine performance and avoid possible damage to after-treatment device 18 and/or other components of regeneration system 16. For example, regeneration device 25 may be configured to cause at least some of the particulate matter that may have accumulated in after-treatment device 18 to be burned off.

Figure 2:
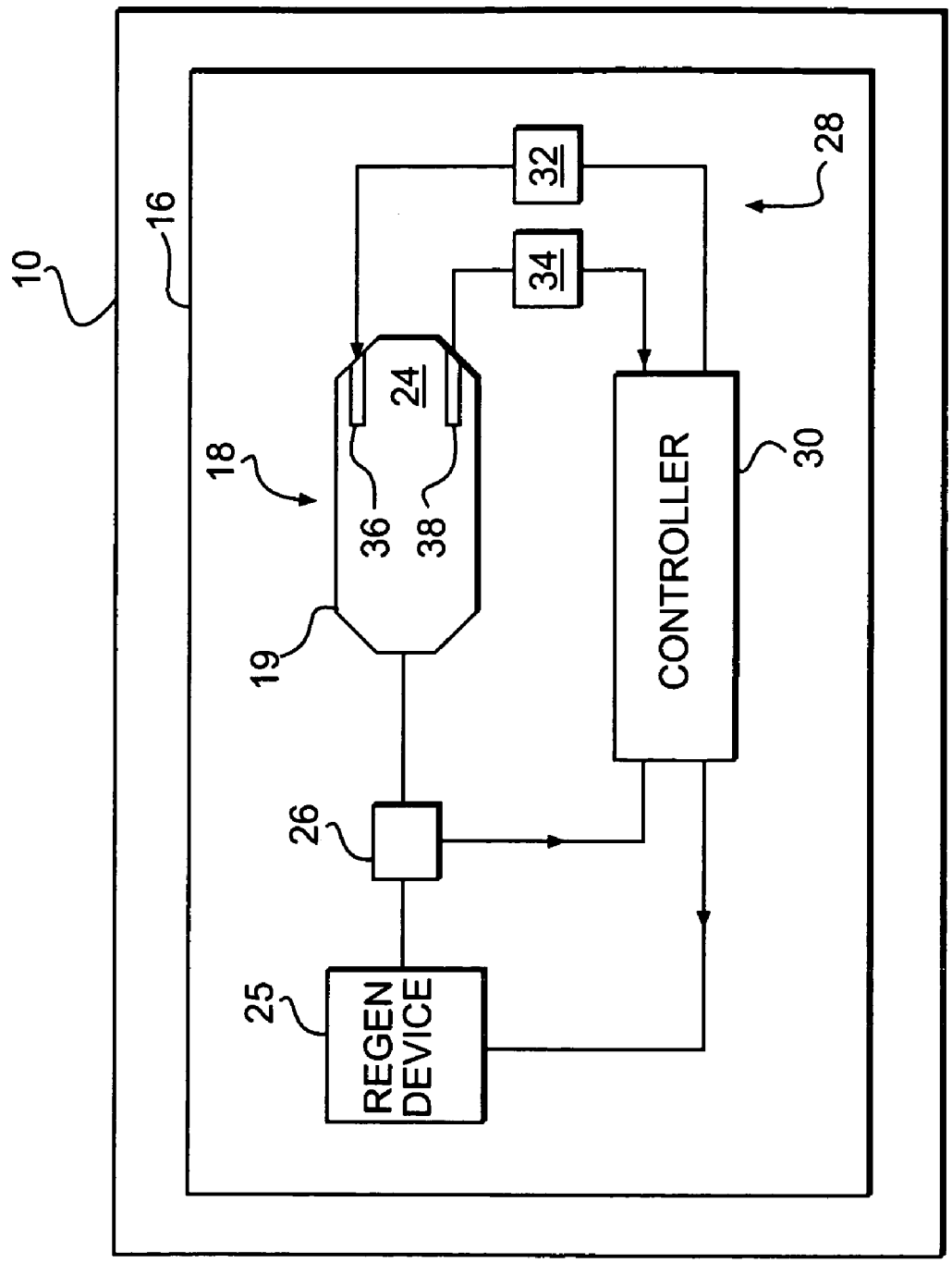
FIG. 2 is a block diagram representation of an exemplary machine including an exemplary disclosed regeneration system and an exemplary disclosed radio frequency particulate sensing system.

FIG. 2 is a block diagram representation of machine 10 including regeneration system 16. Regeneration system 16 may include a temperature sensor 26, which may be configured to facilitate determination of the temperature in after-treatment device 18 (and therefore temperature of filter medium 24). In some embodiments, temperature sensor 26 may be located upstream from after-treatment device 18, as shown in FIG. 2. In other embodiments, temperature sensor 26 may be located downstream of after-treatment device 18. As a further alternative, temperature sensor 26 maybe located on or in after-treatment device 18. Some embodiments may feature more than one temperature sensor, including, for example, sensors located in any of the various locations discussed above.

In addition, regeneration system 16 may include a radio frequency particulate sensing system 28, configured to determine an amount of particulate matter accumulated in filter medium 24. Particulate sensing system 28 will be discussed in further detail below.

Regeneration system 16 may also include a controller 30. Controller 30 may include any means for receiving machine operating parameter-related information and/or for monitoring, recording, storing, indexing, processing, and/or communicating such information. These means may include components such as, for example, a memory, one or more data storage devices, a central processing unit, or any other components that may be used to run an application.

Although aspects of the present disclosure may be described generally as being stored in memory, one skilled in the art will appreciate that these aspects can be stored on or read from types of computer program products or computer-readable media, such as computer chips and secondary storage devices, including hard disks, floppy disks, optical media, CD-ROM, or other forms of RAM or ROM. Various other known circuits may be associated with controller 30, such as power supply circuitry, signal-conditioning circuitry, solenoid driver circuitry, communication circuitry, and other appropriate circuitry.

Controller 30 may perform multiple processing and controlling functions, such as, for example, engine management (e.g., controller 30 may include an engine control module, a.k.a. an ECM), monitoring of particulate loading, and controlling regeneration of after-treatment device 18. For example, controller 30 may be configured to receive the signals detected by a receive circuit or information about such signals. Controller 30 may be further configured to activate regeneration device 25 in response to particulate sensing system 28 detecting more than a predetermined amount of particulate matter trapped in filter medium 24.

Particulate sensing system 28 may include after-treatment device 18, which may include filter medium 24, as discussed above. Particulate sensing system 28 may also include a transmit circuit 32 and a receive circuit 34.

The transmit circuit 32 and the receive circuit 34 may function cooperatively to determine a particulate loading of the filter medium 24. The transmit circuit may generate a radio frequency signal that may be directed, at least partially, through the filter medium 24. The receive circuit 34 may detect a portion of the radio frequency signal and determine a power level of the received radio frequency signal. The power level of the received radio frequency signal may be used to estimate a level of particulate matter disposed, or trapped, in the filter medium 24.

A portion of the transmit circuit 32 and/or receive circuit 34 may be disposed adjacent to the filter medium 24. Alternatively, a portion of the transmit circuit 32 and/or the receive circuit 34 may be disposed within the filter medium 24. For example, a transmit antenna 36 and a receive antenna 38 may be disposed adjacent to the filter medium 24.

Figure 3:
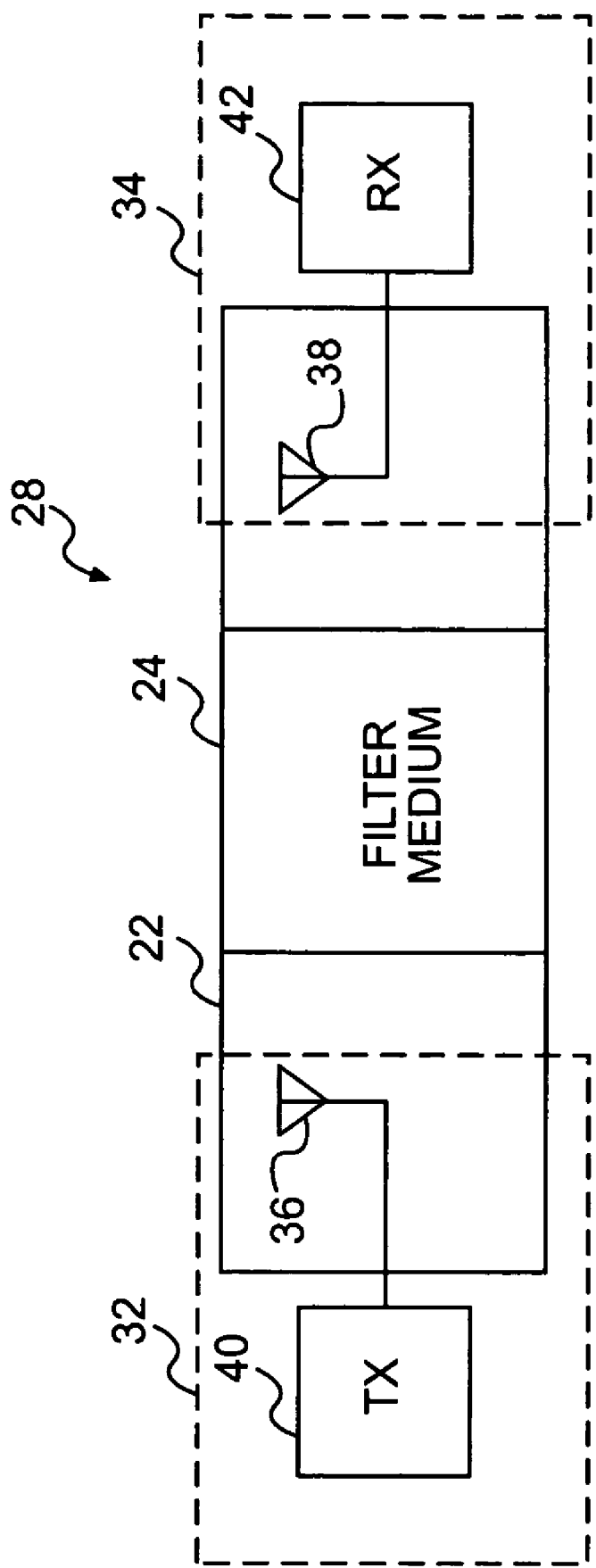
FIG. 3 is a general block diagram representation of an exemplary disclosed radio frequency particulate sensing system.

FIG. 3 is a general block diagram representation of at least some components of an exemplary disclosed embodiment of radio frequency particulate sensing system 28. In addition to components described above in relation to FIG. 2, the transmit circuit 32 may include a transmit module 40 operatively coupled to transmit antenna 36. The receive circuit 34 may include a receive antenna 38 receive module 42 operatively coupled to receive antenna 38.

The transmit module 40 may generate a radio frequency signal that, in turn, may be propagated by the transmit antenna 36 through the filter medium 24. Particulate matter, such as, for example, soot, trapped in or on the filter medium 24 may attenuate the radio frequency signal. The receive antenna 38 may receive the radio frequency signal that has passed through the filter medium 24. The receive module 42 may determine a power level of the received radio frequency signal.

The transmit antenna 36 and the receive antenna 38 may be disposed within outer housing 22 of after-treatment device 18 and adjacent to the filter medium 24 on opposing sides of the filter medium 24. The transmit antenna 36 and the receive antenna 38 may be disposed at opposite ends of the filter medium 24 and parallel to the ends of the filter medium 24. The transmit antenna 36 and receive antenna 38 may be constructed, for example, as wire probes approximately 2.5 inches (65 mm) in length. It should be appreciated that various antenna designs and configurations may be used depending on a contemplated use of the disclosed invention. For example, in a high frequency application the transmit antenna 36 and the receive antenna 26 may be placed about 1 or 2 inches from the filter medium. In another example, the transmit antenna 36 and/or the receive antenna 26 may be placed in the filter medium 24 in a low frequency application.

Figure 4:
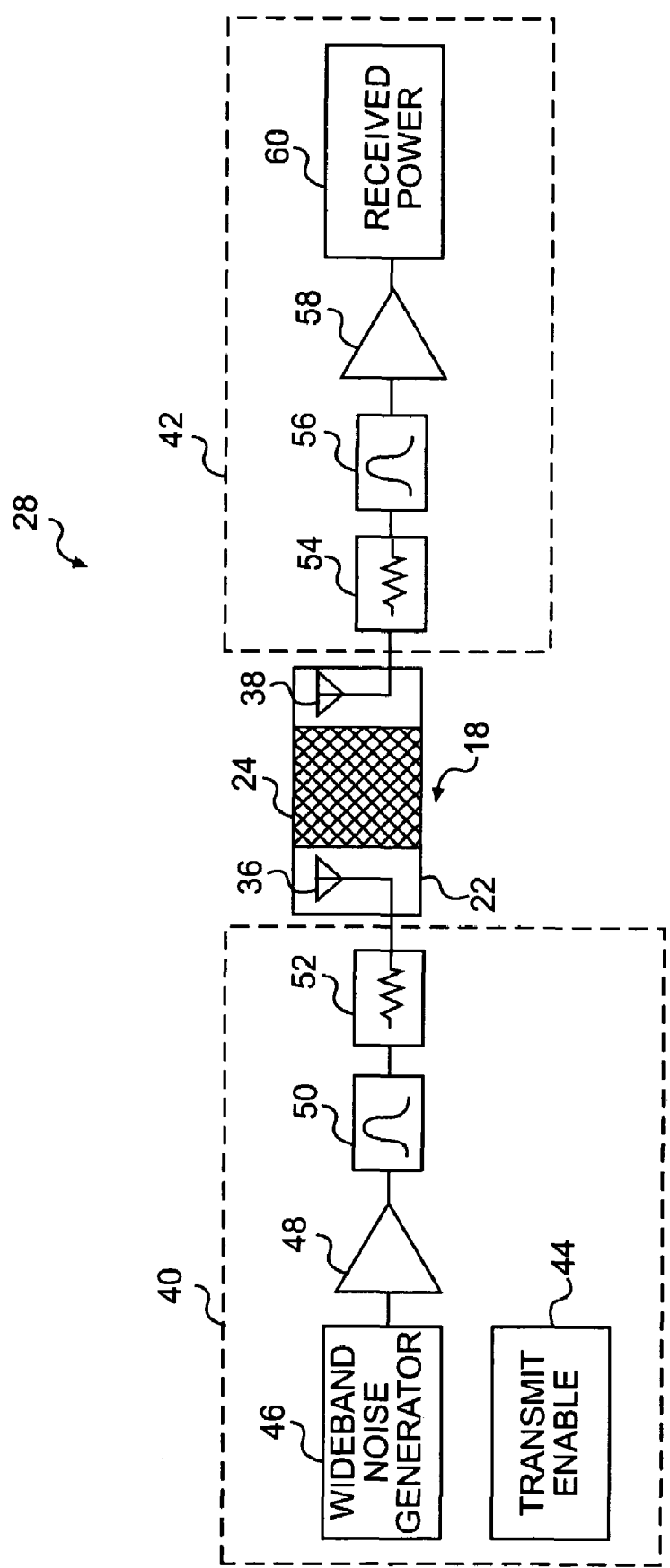
FIG. 4 is a detailed block diagram representation of an exemplary disclosed radio frequency particulate sensing system according to a first embodiment.

FIG. 4 is a detailed block diagram representation of an exemplary disclosed radio frequency particulate sensing system using a wideband radio frequency signal. In particular, the transmit module 40 may include a transmit enable circuit 44, a wideband noise generator 46, a wideband amplifier 48, a transmit bandpass filter 50, and a transmit attenuator 52. The receive module 42 may include a receive attenuator 54, a receive bandpass filter 56, a radio frequency power sensing device 58, and a received power signal terminal 60.

The receive antenna 38 may receive a portion of the wideband radio frequency signal that passed through the filter medium 24. The receive antenna 38 is connected to the receive attenuator 54. The receive attenuator 54 is an optional component. A receive bandpass filter 56 is connected to the receive attenuator 54 and may reduce effects of signal frequencies outside a desired range. The radio frequency power sensing device 58 is connected to the receive bandpass filter 56. The radio frequency power sensing device 58 may include, for example, a logarithmic amplifier that outputs a direct current (DC) voltage proportional to the $\log_{10}$ of the total power received throughout the operating frequency range of the radio frequency power sensing device 58. The DC voltage may be output to an external device via received power signal terminal 60.

The narrowband radio frequency signal propagated through the filter medium may be received using the receive antenna. The bandpass filter may limit a frequency range of the received narrowband radio frequency signal. A power level of the received narrowband radio frequency signal may be sensed using the radio frequency power sensing device. An output signal proportional to the total power received across an operating frequency range of the radio frequency power sensing device may be provided by the radio frequency power sensing device. The output signal from the radio frequency power sensing device may be integrated using the low pass filter, and an analog signal may be produced representing received radio frequency power using the sample-and-hold circuit. The analog signal may be provided, for example, to a machine monitoring system.

The receive antenna 38 may receive a portion of the wideband radio frequency signal that passed through the filter medium 24. The receive antenna 38 is connected to the receive attenuator 70. The receive attenuator 70 is an optional component. A receive bandpass filter 72 is connected to the receive attenuator 70 and may reduce effects of signal frequencies outside a desired range. The radio frequency power sensing device 74 is connected to the receive bandpass filter 72. The radio frequency power sensing device 74 may include, for example, a logarithmic amplifier that outputs a direct current (DC) voltage proportional to the $\log_{10}$ of the total power received throughout the operating frequency range of the radio frequency power sensing device 74. The DC voltage may be output to an external device via received power signal terminal 60.

Figure 5:
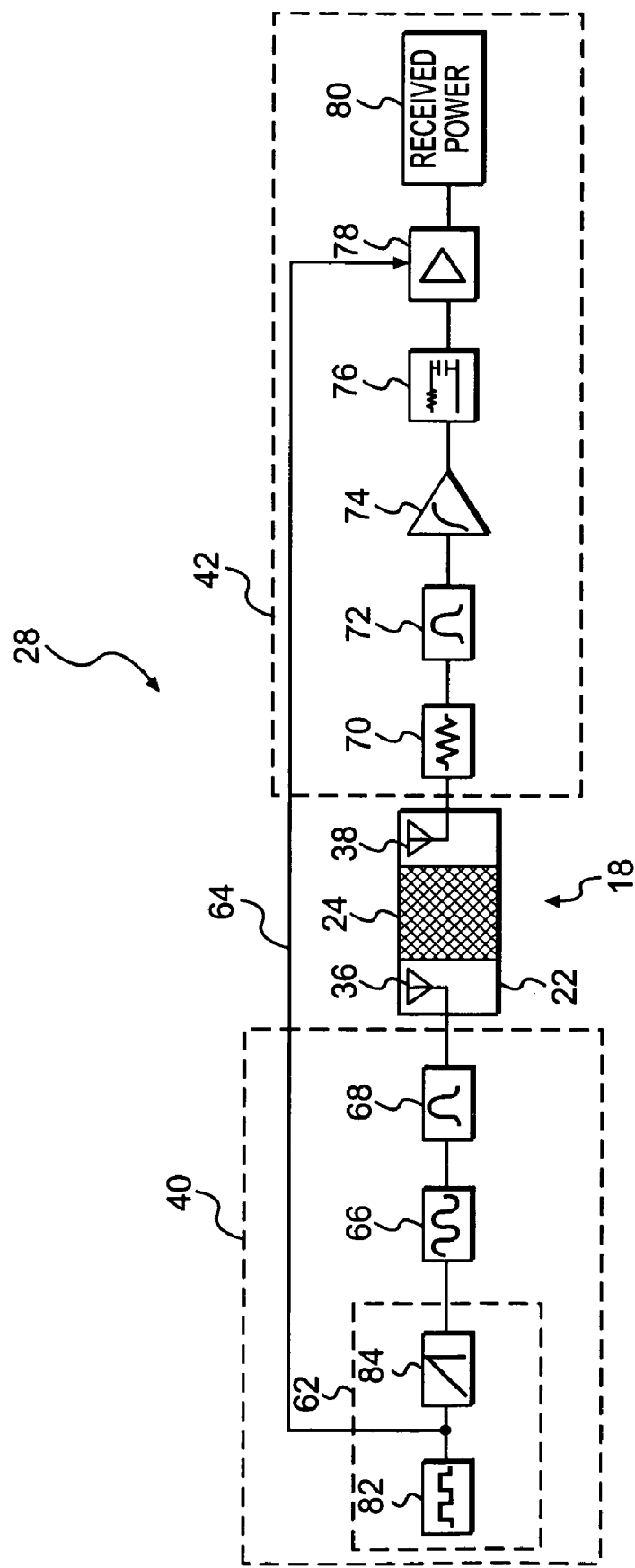
FIG. 5 is a detailed block diagram representation of an exemplary disclosed radio frequency particulate sensing system according to a second embodiment.

FIG. 5 is a detailed block diagram representation of a second embodiment of radio frequency particulate sensing system 28. In this embodiment the transmit module 40 may include a waveform generator 62, a sample trigger line 65, a voltage controlled oscillator (VCO) 66, and a transmit bandpass filter 68. The receive module 42 may include a receive attenuator 70, a bandpass. filter 72, a radio frequency power sensing device 74, a low pass filter 76, a sample-and-hold circuit 78, and a received power terminal 80. The waveform generator 62 may include a timing circuit 82 and a monostable ramp function generator 84. Alternatively, the waveform generator may comprise a microcontroller.

In operation, the timing circuit 82 may provide a timing signal to the monostable ramp function generator 84. The monostable ramp function generator may provide a ramp waveform signal to the VCO 66 which may generate a radio signal having a frequency that is proportional to the received waveform signal. The radio frequency signal may have a frequency in the range of about 550 MHz to about 900 MHz. It should be appreciated that other frequencies and/or frequency ranges may be used depending upon a contemplated use of the disclosed invention. The radio frequency signal may be sent through an optional bandpass filter 68 and then on to the transmit antenna 36. The radio frequency signal may be propagated by the transmit antenna 36 through at least a portion of the filter medium 24.

A portion of the radio frequency signal may pass through the filter medium and reach the receive antenna 38. The receive attenuator 70 (optional) may attenuate the received radio frequency signal. The receive attenuator 70 is coupled to the radio frequency power sensing device 74. The radio frequency power sensing device 74 may include, for example, a logarithmic amplifier that provides an output signal in the form of a direct current (DC) voltage signal proportional to the logo of the total power received throughout the operating frequency range of the radio frequency power sensing device 74. The radio frequency power sensing device 74 may be connected to the low pass filter 76. The low pass filter 76 may include, for example, a resistor-capacitor (RC) integrator. The low pass filter 76 may be connected to the sample-and-hold circuit 78. The sample trigger line 65 may also be connected to the sample-and-hold circuit 78. A sample trigger signal may be sent via the sample trigger line 65 to cause the sample-and-hold circuit 78 to sample the DC voltage and hold the sampled value. The sampled value may be provided to the received power terminal 80 for output to an external device, for example.

Referring again to FIG. 2, in some embodiments that are discussed in more detail in pending U.S. patent application Ser. No. 11/393,681, particulate sensing system 28 may include an upstream temperature sensor (e.g., temperature sensor 26) or any other temperature sensing device, which may be configured to take a temperature measurement indicative of a temperature of after-treatment device 18. Such temperature measurements may be taken in a manner suitable for determining the temperature of after-treatment device 18 at the time the radio signals are received by receive circuit 34. Controller 30 may be configured to determine, based on the measured magnitude of radio frequency signals received by receive circuit 34, a particulate loading value indicative of the amount of particulate matter trapped in filter medium 24. Controller 30 may also be configured to perform a temperature compensation, which may include modifying, based on the temperature measurement, at least one of the following: the measured magnitude of the received radio frequency signals that pass through filter medium 24 or the particulate loading value. In embodiments configured to determine a signal loss value, the signal loss value may be modified to facilitate the temperature compensation.

The temperature compensation may involve a function that is based on the temperature measurement and at least one of the following: the measured magnitude of the received radio frequency signals that pass through filter medium 24 or the particulate loading value. In some embodiments the function may be based on a signal loss value. Further, in some embodiments, the function may be a third order polynomial. That is, the determination of actual particulate loading may be a function of the temperature measurement and observed particulate loading, which may be represented by the measured magnitude of the received radio frequency signals that pass through filter medium 24, the signal loss value, and/or the particulate loading value. Alternatively, the temperature compensation may involve a look-up table based on the temperature measurement and observed particulate loading, as represented by the aforementioned values.

Figure 6:
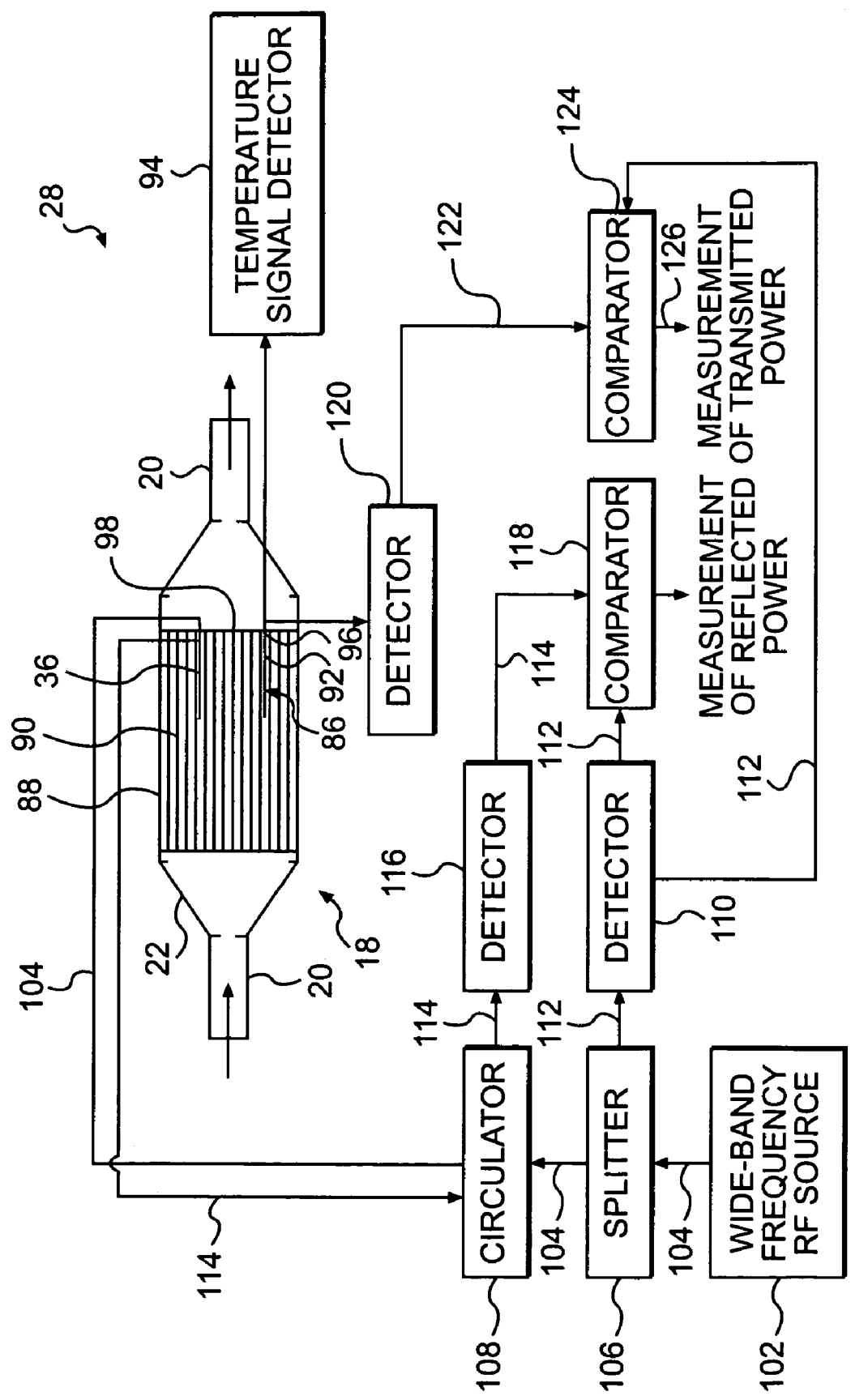
FIG. 6 is a diagrammatic, partial block diagram representation of an exemplary disclosed radio frequency particulate sensing system according to a third embodiment.

In some embodiments that are discussed in more detail in pending U.S. patent applications Ser. Nos. 11/189,530 and 11/355,867, the entire disclosures of which are incorporated herein by reference, particulate sensing system 28 may include a receiving sensor 86, which acts in the dual capacity of a thermocouple and antenna. An example of such an embodiment is illustrated in FIG. 6. As shown in FIG. 6, particulate sensing system 28 may include after-treatment device 18, which may include outer housing 22. Outer housing 22 may define a chamber 88 configured to receive a filter element 90 of suitable construction. Transmit antenna 36 may be configured to transmit a RF signal and receiving sensor 86 may be configured to receive RF signal that passes through filter element 90. As shown in FIG. 6 (and illustrated in more detail in FIG. 7), receiving sensor 86 may include a thermocouple 92, which may be configured to deliver a signal indicative of temperature within filter element 90 to a temperature signal detector 94. In certain embodiments, transmit antenna 36, receiving sensor 86 may be disposed within housing 10 and may be embedded within filter element 90. Although FIG. 6 illustrates transmit antenna 36 and receiving sensor 86 as being embedded in filter element 90, the reader should appreciate that transmit antenna 36 and receiving sensor 86 may be positioned outside filter element 90 and, in some cases, outside outer housing 22.

Figure 7:
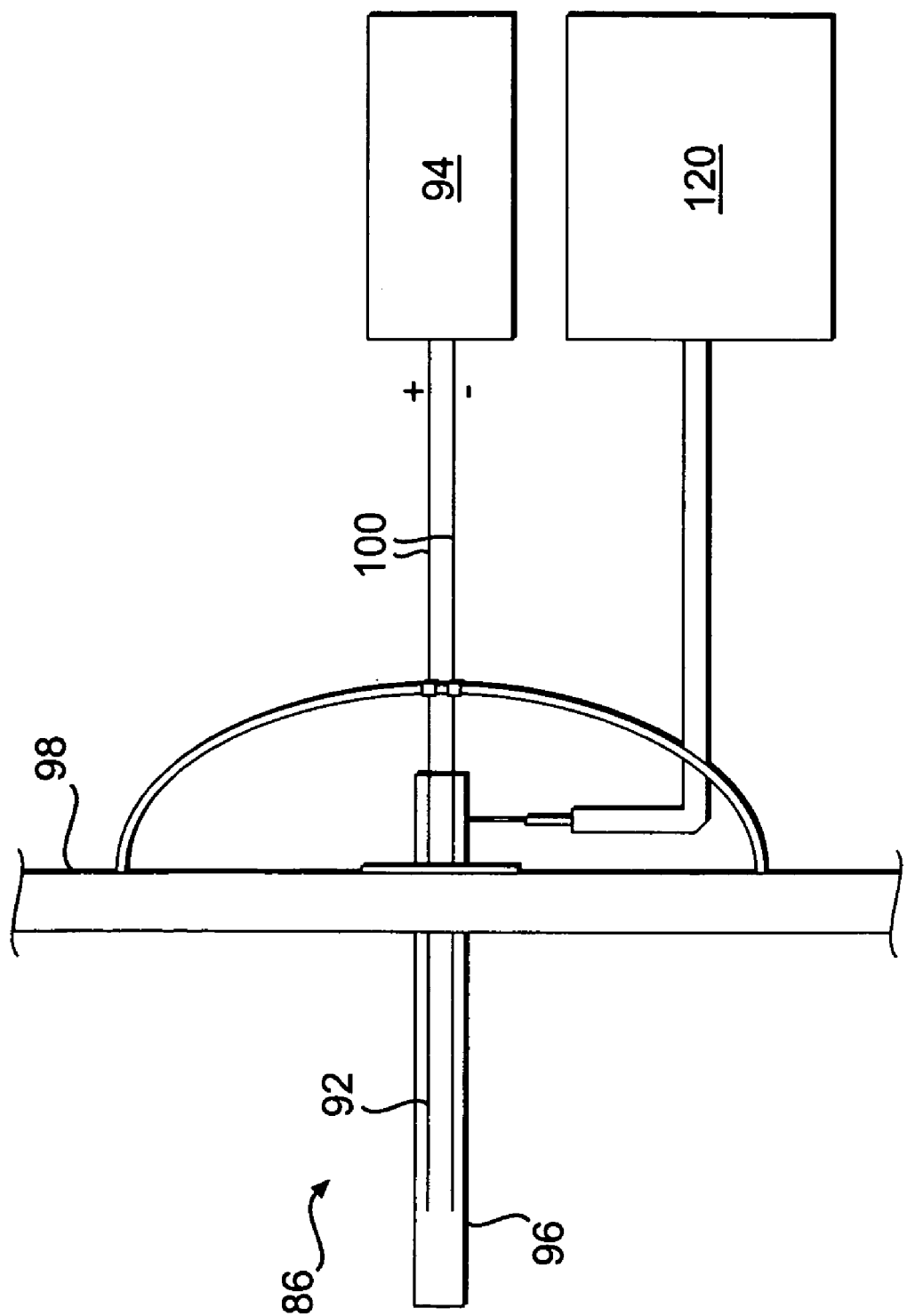
FIG. 7 is a diagrammatic representation of a receiving sensor including a receiving antenna and a thermocouple according to the third embodiment shown in FIG. 6.

FIG. 7 illustrates an embodiment, which is described in more detail in U.S. patent application Ser. No. 11/355,867. FIG. 7 depicts receiving sensor 86, which may include both a thermocouple 92 and a receiving antenna 96. As can be seen, the combined thermocouple/antenna sensor 86 requires only one protrusion through filter wall 98—as opposed to a separate thermocouple and antenna arrangement, which would require two separate protrusions.

Furthermore, although FIG. 6 depicts RF signal receiving sensor 86 as including a thermocouple (92), it should be noted that, alternatively or additionally, transmit antenna 36 may include a thermocouple, which may be associated with a temperature signal detector (e.g., temperature signal detector 94).

A traditional thermocouple may simply include a resistive thermistor housed in a heat-compatible metal sheath. Some metal sheaths may be manufactured, in part, with iconel. The resistive thermistor is typically kept electronically separate from the metal sheath to prevent the sheath from providing a ground to one of two thermocouple wires 100. If one or both of the wires 100 contact the metal sheath, the thermocouple 92 may provide an erroneous temperature indication.

A traditional antenna, on the other hand, is generally a solid wire or hollow tube, which sends, receives, or transceives RF signals. FIG. 7 illustrates a thermocouple 92 housed within a hollow tube receiving antenna 96. The combined thermocouple 92 and receiving antenna 96 make up sensor 86. In this embodiment, sheath/antenna 70 performs the dual function of thermocouple sheath and antenna and thermocouple 92 wires 100 perform the function of measuring temperature. In this embodiment, wires 100 are maintained electrically separate from sheath/antenna 96. With wires 100 housed within sheath/antenna 96, as depicted, only one physical intrusion is required through filter wall 98.

In some embodiments, which are described in more detail in U.S. patent application Ser. No. 11/189,530, reflected RF power may be detected in addition to transmitted power to determine a level of particulate accumulation in filter medium 24. FIG. 6 shows an exemplary system configured to monitor reflected RF power. As shown in FIG. 6, such embodiments may include a wide-band frequency source 102, which may generate a source signal 104 and apply source signal 104 to a splitter 106. Splitter 106 may apply source signal 104 to both a circulator 108 and a first detector 110. First detector 110 may produce a reference output signal 112 that is representative of the power of source signal 104 prior to transmission through filter medium 24.

As mentioned, wide-band frequency source 102 may supply source signal 104 to splitter 106, which may send reference output signal 112 of source signal 104 to first detector 110. The remainder of source signal 104 may be passed through circulator 108 to transmit antenna 36, which, in the illustrated embodiment, may be inserted into filter medium 24. Depending on several factors, including antenna design, the frequency of source signal 104, and the combined dielectric properties of filter medium 24 and the particulate matter accumulated therein, some of the RF power of signal 104 may be reflected back to circulator 108. In this embodiment, circulator 108 may be a directional coupler and a reflected power signal 114 may be directed to a second detector 116. Reflected power signal 114 directed to second detector 116 may then be sent to a first comparator 118. First comparator 118 may compare reflected power signal 114 to reference output signal 112, which was sent to comparator 118 from detector 110. First comparator 118 may include circuitry configured to make such a comparison, including, for example, a differential amplifier (not shown). The ratio of reflected power signal 114 to reference source signal 112 may provide a relative measurement of the power reflected by the combined dielectric characteristics (i.e., the effective dielectric constant) of filter medium 24 and the particulate matter collected therein.

Similarly, the RF power from source signal 104 that is transmitted by transmit antenna 36 through filter medium 24 and the particulate matter collected therein may be measured by a receiving antenna 96 (which, although illustrated in FIGS. 6 and 7 as including a thermocouple, may be provided as a separate component and, in some embodiments the thermocouple may be omitted altogether) and a signal detector 120. A transmitted RF power signal 122 may be sent to a second comparator 124, which may compare the transmitted RF power signal 122 to reference output signal 112 from first detector 110. Second comparator 124 may include circuitry configured to make such a comparison, including, for example, a differential amplifier (not shown). The relative transmitted power signal thus measured is a unique function of the frequency of the transmitted power, the design of transmit antenna 36 and receiving antenna 96, and the dielectric properties of filter medium 24 and the particulate matter collected therein. The strength of this latter signal at any frequency is equal to the relative strength of the source signal 104 minus the sum of the reflected power signal 114 (a function of the effective dielectric constant)

and the amount of adsorbed RF power (a function of the effective dielectric loss factor).

Accordingly, second comparator 124 may produce an output signal 126, which is representative of the transmission loss through filter medium 24, which, in turn, is representative of the change in the effective dielectric constant and loss factor caused by accumulation of particulate matter within filter medium 24. It will be seen therefore that when there is little or no accumulation in filter medium 24, there will be only a small transmission loss in the strength of source signal 104. As the accumulation of particulate matter increases within filter medium 24, the difference in signal strength between source signal 104 and transmitted signal 122 changes, resulting in output signal 126 from second comparator 124. Second comparator 124 can be designed to drive a variable output display or an indication when a predetermined level is reached, or both.

Industrial Applicability

The disclosed radio frequency particulate sensing system may be applicable to any machine that includes a particulate trap. The disclosed radio frequency particulate sensing system may provide a measurement of particulate loading within a particulate filter medium such that the particulate trap may be cleaned, regenerated, or replaced.

The disclosed particulate trap regeneration system 16 may be suitable to enhance exhaust emissions control for engines by using the disclosed particulate sensing system. Regeneration system 16 may be used for any application of an engine. Such applications may include, for example, stationary equipment such as power generation sets, or mobile equipment, such as vehicles. The disclosed system may be used for any kind of vehicle, such as, for example, automobiles, machines (including those for on-road, as well as off-road use), and other heavy equipment.

Several advantages over the prior art may be associated with the disclosed radio frequency particulate sensing system. For example, the disclosed radio frequency particulate sensing system may provide a simplified radio frequency particulate sensing system that may not require a microprocessor, frequency synthesizer and/or associated components in order to generate the radio frequency signal. Also, the disclosed radio frequency particulate sensing system may be operated using a wideband radio frequency signal that may provide for a simplified circuit.

The disclosed radio frequency particulate sensing system may be used on a machine by providing a radio frequency transmit circuit including a waveform generator, a sample trigger line, a voltage controlled oscillator, and a transmit antenna. Also, a radio frequency receive circuit may be provided, the receive circuit may include a receive antenna, a bandpass filter, a radio frequency power sensing device, a low pass filter, and a sample-and-hold circuit.

One or more waveform signals may be generated using the waveform generator. The waveform generator may include a timing circuit for generating a timing pulse signal and a ramp function signal using a monostable ramp function generator coupled to the timing circuit and triggered using the timing pulse signal as a ramp trigger. A sample trigger signal may be transmitted to the sample-and-hold circuit using the sample trigger line. Alternatively, a microcontroller may be used to, generate the waveform signal. A narrowband radio frequency signal may be generated based on the waveform signal using the voltage controlled oscillator. The narrowband frequency signal may include a frequency in the range of about 550 MHz to about 900 MHz. The narrowband radio frequency signal may be filtered using a bandpass filter disposed in the radio frequency transmit circuit between the voltage controlled oscillator and the transmit antenna. The narrowband radio frequency signal may be propagated through a filter medium using the transmit antenna.

The narrowband radio frequency signal propagated through the filter medium may be received using the receive antenna. The bandpass filter may limit a frequency range of the received wideband radio frequency signal. A power level of the received narrowband radio frequency signal may be sensed using the radio frequency power sensing device. An output signal proportional to the total power received across an operating frequency range of the radio frequency power sensing device may be provided by the radio frequency power sensing device. The output signal from the radio frequency power sensing device may be integrated using the low pass filter, and an analog signal may be produced representing received radio frequency power using the sample-and-hold circuit. The analog signal may be provided, for example, to a machine monitoring system.

Figure 8:
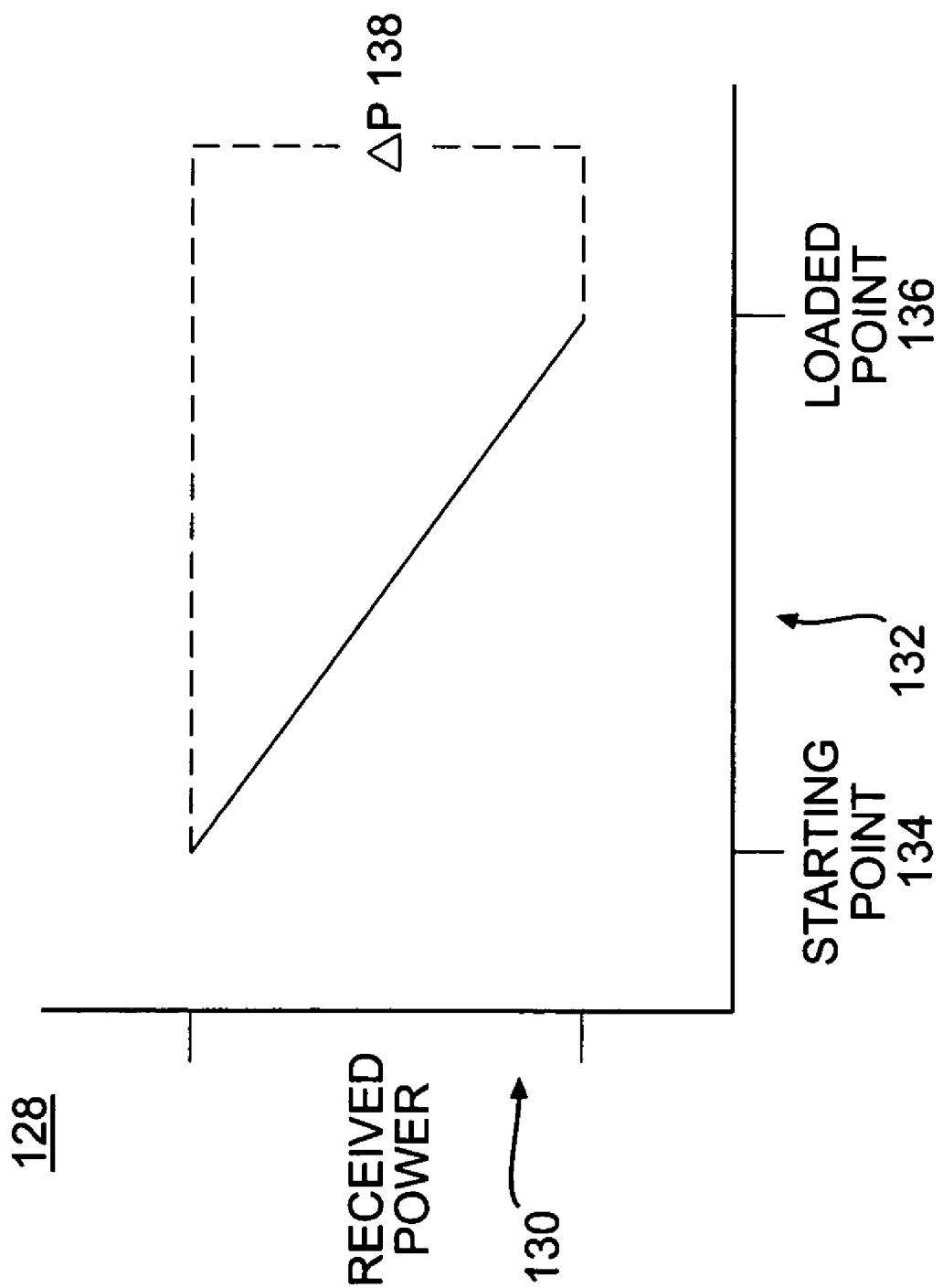
FIG. 8 is a graph of an exemplary received power signal in accordance with a disclosed radio frequency particulate sensing system.

FIG. 8 is a graph 128 of an exemplary received power signal in accordance with a disclosed radio frequency particulate sensing system. In particular, received power 130 is represented by the vertical axis and measured particulate loading 132 is represented on the horizontal axis. A starting point 134 measurement is taken, for example, when a new, or clean, particulate trap is installed on a machine. As the machine operates and the particulate trap collects particulate matter, the received power may diminish. A loaded point 136 of the filter medium may represent a condition in which the received power has diminished by a predetermined change in power ($\Delta P$) 138. Once the change in power 138 has been reached, a machine monitoring system may take an appropriate response action, including, for example, illuminating an indicator light for an operator, initiating an automatic filter cleaning process (if available), and/or storing or transmitting an indication that the particulate trap needs servicing.

It will be apparent to those skilled in the art that various modifications and variations can be made to the disclosed radio frequency particulate sensing system. Other embodiments will be apparent to those skilled in the art from consideration of the specification and practice of the disclosed radio frequency particulate sensing system. It is intended that the specification and examples be considered as exemplary only, with a true scope being indicated by the following claims and their equivalents.

What is claimed is:

1. A particulate sensing system for a particulate trap comprising:
    a radio frequency transmit circuit including:
        a wideband signal generator for producing a wideband radio frequency signal;
        a wideband radio frequency amplifier coupled to the wideband signal generator and configured to amplify the wideband radio frequency signal; and
        a transmit antenna coupled to the wideband radio frequency amplifier and configured to propagate the wideband radio frequency signal through a particulate filter medium;
    a radio frequency receive circuit including:
        a receive antenna configured to receive the wideband radio frequency signal that has been propagated through the filter medium;
        a bandpass filter coupled to the receive antenna and configured to limit a frequency range of the received wideband radio frequency signal; and a radio frequency power sensing device coupled to the bandpass filter and configured to sense a power level of the received wideband radio frequency signal and configured to output a direct current voltage proportional to the total power received across an operating frequency range of the radio frequency power sensing device.

2. The system of claim 1, wherein a frequency range of the wideband radio frequency signal is from about 550 MHZ to about 900 MHz.

3. The system of claim 1, wherein the transmit antenna is disposed in a filter body containing the filter medium and adjacent to the filter medium, and the receive antenna is disposed in the filter body and adjacent to the filter medium on a side of the filter medium opposing the transmit antenna.

4. The system of claim 1, wherein the wideband signal generator is one of a wideband harmonic generator or a wideband noise source.

5. The system of claim 4, wherein the wideband signal generator is a zener diode.

6. The system of claim 4, wherein the wideband signal generator is a wideband comb generator.

7. The system of claim 1, further including a transmit enable circuit coupled to the wideband signal generator, the transmit enable circuit configured to cause the wideband signal generator to operate periodically.

8. The system of claim 1, further including a transmit bandpass filter coupled to the wideband amplifier and the transmit antenna.

9. The system of claim 1, further including an attenuator disposed between the wideband amplifier and the transmit antenna.

10. The system of claim 1, further including an attenuator disposed between the receive antenna and the bandpass filter.

11. A particulate sensing system for a particulate trap comprising:
a particulate trap including a filter body and a filter medium;
a radio frequency transmit circuit including:
a waveform generator configured to generate at least one waveform signal;
a sample trigger line coupled to the waveform generator and configured to provide a sample trigger signal;
a voltage controlled oscillator coupled to the waveform generator and configured to produce a narrowband radio signal having a frequency that is proportional to the waveform signal;
a transmit antenna disposed within the filter body and adjacent to the filter medium and coupled to the voltage controlled oscillator, the transmit antenna configured to propagate the narrowband radio frequency signal through the filter medium;
a radio frequency receive circuit including:
a receive antenna, disposed in the filter body opposing the transmit antenna and adjacent to the filter medium, the receive antenna configured to receive the narrowband radio frequency signal propagated through the filter medium;
a bandpass filter coupled to the receive antenna and configured to limit a frequency range of the received narrowband radio frequency signal;
a radio frequency power sensing device coupled to the bandpass filter and configured to sense a power level of the received narrowband radio frequency signal and configured to provide an output signal proportional to the total power received across an operating frequency range of the radio frequency power sensing device;
a low pass filter coupled to the radio frequency power sensing device and configured to integrate the output signal; and
a sample-and-hold circuit coupled to the low pass filter and the sample trigger line, the sample-and-hold circuit configured to sample an output of the low pass filter using the sample trigger signal, hold the sampled value, and produce an analog signal representing received radio frequency power.

12. The system of claim 11, wherein a frequency range of the narrowband radio frequency signal is from about 550 MHZ to about 900 MHz.

13. The system of claim 11, wherein the waveform generator includes a timing circuit for generating a timing pulse signal and a monostable ramp function generator coupled to the timing circuit and triggered using the timing pulse signal as a ramp trigger.

14. The system of claim 11, wherein the waveform generator includes a microcontroller for generating the waveform signal.

15. The system of claim 11, further including a transmit bandpass filter coupled to the voltage controlled oscillator and the transmit antenna.

16. The system of claim 11, further including an attenuator disposed between the receive antenna and the bandpass filter.

17. A method of sensing particulate matter in a particulate trap, the method comprising:
providing a radio frequency transmit circuit including a waveform generator, a sample trigger line, a voltage controlled oscillator, and a transmit antenna;
generating at least one waveform signal using the waveform generator;
providing a sample trigger signal using the sample trigger line;
producing a narrowband radio frequency signal based on the waveform signal using the voltage controlled oscillator;
propagating the narrowband radio frequency signal through a filter medium of the particulate trap using the transmit antenna;
providing a radio frequency receive circuit including a receive antenna, a bandpass filter, a radio frequency power sensing device, a low pass filter, and a sample-and-hold circuit;
receiving the narrowband radio frequency signal propagated through the filter medium using the receive antenna;
limiting a frequency range of the received narrowband radio frequency signal using the bandpass filter;
sensing a power level of the received narrowband radio frequency signal using the radio frequency power sensing device;
providing an output signal proportional to the total power received across an operating frequency range of the radio frequency power sensing device;
integrating the output signal using the low pass filter; and
producing an analog signal using the sample-and-hold circuit, the analog signal representing received radio frequency power.

18. The method of claim 17, wherein producing a narrowband radio frequency signal includes producing a signal having a frequency range of about 550 MHz to about 900 MHz.

19. The method of claim 17, wherein generating a waveform signal includes using a timing circuit for generating a timing pulse signal and a generating a ramp function signal using a monostable ramp function generator coupled to the timing circuit and triggered using the timing pulse signal as a ramp trigger.

20. The method of claim 17, wherein generating a waveform signal includes using a microcontroller for generating the waveform signal.

21. The method of claim 17, further including filtering the narrowband radio frequency signal using a bandpass filter disposed in the radio frequency transmit circuit between the voltage controlled oscillator and the transmit antenna.

22. The method of claim 17, further including providing the analog signal to a machine monitoring system.

* * * * *